US006810391B1

(12) United States Patent
Birkhoelzer et al.

(10) Patent No.: US 6,810,391 B1
(45) Date of Patent: Oct. 26, 2004

(54) SYSTEM FOR CALCULATING ANALYTICAL DATA AND MAKING CALCULATION RESULTS AVAILABLE AS AN OUTPUT

(75) Inventors: Thomas Birkhoelzer, Weisendorf (DE); Joachim Horn, Munich (DE); Marco Pellegrino, Vaterstetten (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/388,627

(22) Filed: Sep. 2, 1999

(30) Foreign Application Priority Data

Sep. 14, 1998 (DE) .......................................... 198 42 046

(51) Int. Cl.[7] .............................. G06F 15/18; A61B 5/00
(52) U.S. Cl. ............................... 706/8; 706/16; 706/45; 706/50; 706/60; 706/924; 128/904; 128/924; 600/300
(58) Field of Search ............................... 706/50, 8, 20, 706/16, 60, 924, 934, 9, 48, 15, 45; 600/300; 128/904, 924

(56) References Cited

U.S. PATENT DOCUMENTS

| | | | | |
|---|---|---|---|---|
| 5,357,427 A | * | 10/1994 | Langen et al. ............... | 600/300 |
| 5,471,382 A | * | 11/1995 | Tallman et al. ............. | 600/300 |
| 5,574,828 A | * | 11/1996 | Hayward et al. ............. | 706/45 |
| 5,664,066 A | * | 9/1997 | Sun et al. ...................... | 706/25 |
| 5,720,007 A | | 2/1998 | Hekmatpour ................. | 706/50 |
| 5,769,074 A | * | 6/1998 | Barnhill et al. ............. | 600/300 |
| 5,810,747 A | * | 9/1998 | Brudny et al. ............... | 600/595 |
| 5,839,438 A | * | 11/1998 | Graettinger et al. ........ | 600/300 |
| 5,922,079 A | * | 7/1999 | Booth et al. .................. | 714/26 |
| 6,007,491 A | * | 12/1999 | Ling et al. .................... | 600/481 |
| 6,083,173 A | * | 7/2000 | Grant et al. .................. | 600/529 |
| 6,248,063 B1 | * | 6/2001 | Barnhill et al. ............. | 600/300 |
| 6,267,722 B1 | * | 7/2001 | Anderson et al. ........... | 600/300 |
| 6,334,192 B1 | * | 12/2001 | Karpf ............................. | 714/1 |
| 6,394,952 B1 | * | 5/2002 | Anderson et al. ........... | 600/300 |
| 6,496,816 B1 | * | 12/2002 | Thiesson et al. .............. | 706/52 |
| 6,529,891 B1 | * | 3/2003 | Heckerman ................... | 706/52 |
| 2001/0012913 A1 | * | 8/2001 | Iliff ............................. | 600/300 |
| 2002/0107824 A1 | * | 8/2002 | Ahmed ......................... | 706/46 |
| 2003/0036686 A1 | * | 2/2003 | Iliff ............................. | 600/300 |

FOREIGN PATENT DOCUMENTS

DE         OS 44 30 164         2/1996    ............. G06F/3/16

OTHER PUBLICATIONS

Gauch et al., "Search Improvement via Automatic Query Reformulation", ACM Transactions on Information Systems, Jul. 1991 vol. 9, No. 3, pp. 249–280.*

(List continued on next page.)

*Primary Examiner*—Ramesh Patel
*Assistant Examiner*—Kelvin Booker
(74) *Attorney, Agent, or Firm*—Schiff Hardin

(57) ABSTRACT a System for calculating and emitting analytical data, particularly medically relevant analytical data, has a computer with an evaluation unit for analyzing information entered by the system user and for generating the analytical data, and an output medium provided at the user side. The evaluation unit is configured for interrogating and accepting information that can be entered at the user side such that the information can be entered autonomously by the user based on a number of inquiries which are predefined at the system side, and which can be selected with reference to each response, and which can be made available as an output to user via the output medium. The evaluation unit is configured for controlling an interactive information capture such that, depending on the running information compilation, specific inquiries can be formulated and shown to the user. The evaluation unit is configured for processing information that is random in content and for evaluating the analytical data with a value measure lying between two extreme values. The analytical data that is generated on the basis of the running information compilation can be interrogated by the user at any time and supplied to the user as an output upon such interrogation.

20 Claims, 3 Drawing Sheets

OTHER PUBLICATIONS

Doyle et al., "Strategic Directions in Artificial Intelligence", ACM Computing Surveys, Dec. 1996, vol. 28, No. 4, pp. 653 670.*

Ramil et al., "Fuzzy Dynamics in Software Project Simulation and Support", European Workshop on Software Process Technology, 1998, pp. 122–126.*

Herrmann, C.S., "A Hybrid Fuzzy–Neural Expert System for Diagnosis", Proceedings of the International Joint Conference on Artificial Intelligence, 1995.*

Hudson et al., "Human–Computer Interaction in a Medical Decision Support System", Proceedings of the 22nd Annual Hawaii International Conference on System Sciences, Jan. 1989, vol. 2, pp. 429–435.*

Armstrong et al., "An Object–Oriented Medical Decision Support System", IEE Colloquium on Applications and Experience of Object–Oriented Design, Jan. 1991, pp. 1/1–1/3.*

Krause et al., "Can We Formally Specify a Medical Decision Support System?", IEEE Expert, Jun. 1993, vol. 8, Iss 3, pp. 56 61.*

Becker et al., "Fuzzy Logic Approaches to Intelligent Alarms", IEEE Engineering in Medicine and Biology, Nov. 1994, vol. 13, Iss 5, pp. 710–716.*

Chiu et al., "A Complete, Hypermedia Medical Decision Analysis Support System", Proceedings of the 1994 IEEE th Symposiu on Computer–Based Medical Systems, Jun. 1994, pp. 16–21.*

Economou et al., "A Novel Medical Decision Support System", Computing and Control Engineering Journal, Aug. 1996, vol. Iss 4, pp. 177–183.*

Gorzalczany, M.B., "An Idea of the Application of Fuzzy Neural Networks to Medical Decision Support Systems", Proceedings the IEEE International Symposium on Industrial Electronics, Jun. 1996, vol. 1, pp. 398–403.*

Gorzalczany, M.B., "Fuzzy Neural Networks Versus Alternative Approaches in Medical Decision Support", Proceedings of the IEEE International Symposium on Industial Electronics, Jul. 1997, vol. 3, pp. 1270–1275.*

Zhi–Xing et al., "Application of Fuzzy Neural Network to ECG Diagnosis", International Conference on Neural Networks, Jun. 1997, vol. 1, pp. 62–66.*

Gorzalczany et al., "Combination of Neural Networks and Fuzzy Sets as a Basis for Medical Expert Systems", Proceedings of the 5th Annual IEEE Symposium on Computer–Based Medical Systems, Jun. 1992, pp. 412–420.*

Guazzelli et al., "Incorporating Semantics to ART", 1994 IEEE International Conference on Neural Networks, Jun. 1994, vol. 3, pp. 1726–1731.*

Cohen et al., "Combination of a Neural Network Model and a Rule–Based Expert System to Determine Efficacy of Medical Testing Procedures", IEEE Engineering in Medicine and Biology Society 11th Annual International Conference, Nov. 198.*

Schizas et al., "Networks: In Search of Computer–Aided Diagnosis", 1991 IEEE International Joint Conference on Neura Networks, Nov. 1991, vol. 2, pp. 1825–1830.*

Hayashi et al., "Fuzzy Neural Expert Systems with Automated Extraction of Fuzzy If–Then Rules From a Trained Neural Network", 1st International Symposium on Uncertainty Modeling and Analysis, Dec. 1990, pp. 489–494.*

Herrmann, C.S., "Symbolical Reasoning about Numerical Data: A Hybrid Approach", Applied Intelligence, 1997, vol. 7, No. 4, pp. 339–354.*

* cited by examiner

SYSTEM FOR CALCULATING ANALYTICAL DATA AND MAKING CALCULATION RESULTS AVAILABLE AS AN OUTPUT

BACKGROUND OF THE INVENTION

1. Field of the Invention

The present invention relates to a system for calculating and providing analytical data as an output, particularly medical analytical data.

2. Description of the Prior Art

Lay persons, particularly lay persons who are medical patients, require information from experts such as doctors for concrete problems such as health. Such a consultation usually takes place in person; i.e., the person desiring information must visit the expert, for instance the doctor. It is possible to discuss the current problem and the individual situation concretely in the context of such a personal interview. The course of the consultation or the informational interview can be dictated by the participants themselves. Uncertain statements can be followed up and taken into account in the final result, so that it is possible to make and discuss alternative statements. Such a consultation must proceed openly, in the sense that it does not necessarily result in a final decision.

It is not always possible, however, to consult with experts in case of need, and such consultation is relatively costly.

SUMMARY OF THE INVENTION

An object of the present invention is to provide a system of the type initially described which is capable of conveying a specific item of information to the information seeker with respect to a concrete problem, which makes it possible to generate the given information in the form of analytical data, such as occur on the part of the expert in the context of a personal consultation.

This object is achieved in accordance with the invention in a system having a computer with an evaluation unit for analyzing information that can be entered by the system user and for generating analytical data, and an output medium at the user side, the evaluation unit being configured for interrogating and accepting information entered at the user side, both for allowing information to be entered autonomously by the user based on a number of inquiries which are predefined at the system side, and which are selectable with respect to the response, and which can be omitted via the output medium. The evaluation unit also is configured for controlling an interactive information capture so that specific inquiries can be formulated and made available as an output depending on the previous information. The evaluation unit is configured for processing information that is random in content and for evaluating the analytical data with a continuous value measure, so that it is possible for the user to retrieve and output, at any time, the analytical data that can be generated on the basis of previous information.

The inventive system enables the system user to obtain the necessary information by exchanging information with the evaluation unit, or with the system itself. To collect the information required for the generation of the analytical data, the evaluation unit can be operated in various modes of operation. In one mode, questions which are defined at the evaluation unit side are given to the user, who can answer them with "yes" or "no," for example, or, in the case of a system configured for medical problems, by indicating body temperature or the like. In this way, information can be collected which the user himself can recognize and acquire. Compared to a personal consultation, information thus can be captured which the expert collects, for instance the doctor may ask the question "Which symptoms of disease do you have?" to which the patient responds, "skin rash".

In addition, the inventive evaluation system is also capable of formulating questions autonomously, based on the existing information, in order to intentionally solicit information it requires for purposes of generating the analytical data. To this end, the evaluation unit can be an expert system such as a neural network or a Bayes network, for example, the system being configured for generating and formulating corresponding questions that influence the analytical data in some way. Information thus can be collected which are obtained in personal consultation by means of purposeful questioning by the expert, who takes into account his or her expertise, as well as the information already given. The evaluation unit is thus capable of processing information with an arbitrary content; i.e., not only absolute items of information such as "yes" and "no" are processed, but also it is possible to process uncertain statements of information by the user such as "I don't know" or the like. The system is completely open; there are no limitations of any kind relating to the enterable information content, or the type of enterable information.

Another particular advantage of the inventive system is that the evaluation unit is configured to evaluate the analytical data with a value measure. This value measure can be a measure of possibility, for instance, of the type that indicates the likelihood percentage that given analytical data are correct and enables the user to advantageously detect "the weight" of the outputted analytical output data, in order possibly to be able to reach a further decision based thereon. The user thus receives a statement of possibility as to whether, and with what probability, one disease or another may be present, as in a personal consultation. A decision, i.e. stipulating a specific alternative which can be the only one, does not occur. The user can stop the analysis mode at any time and receive the result of the analysis as an output. That is, the system is flexible to the extent that it does not require a specific amount of information to corresponding inquiries. Rather, the analysis can be brought to an end at any time. In sum, the inventive system enables the user to be able to collect a problem-specific consultation result autonomously, with different information being taken into consideration in the consultation result, and the analytical result is open, as is the case in a personal consultation.

DESCRIPTION OF THE PREFERRED EMBODIMENTS

Figure 1:
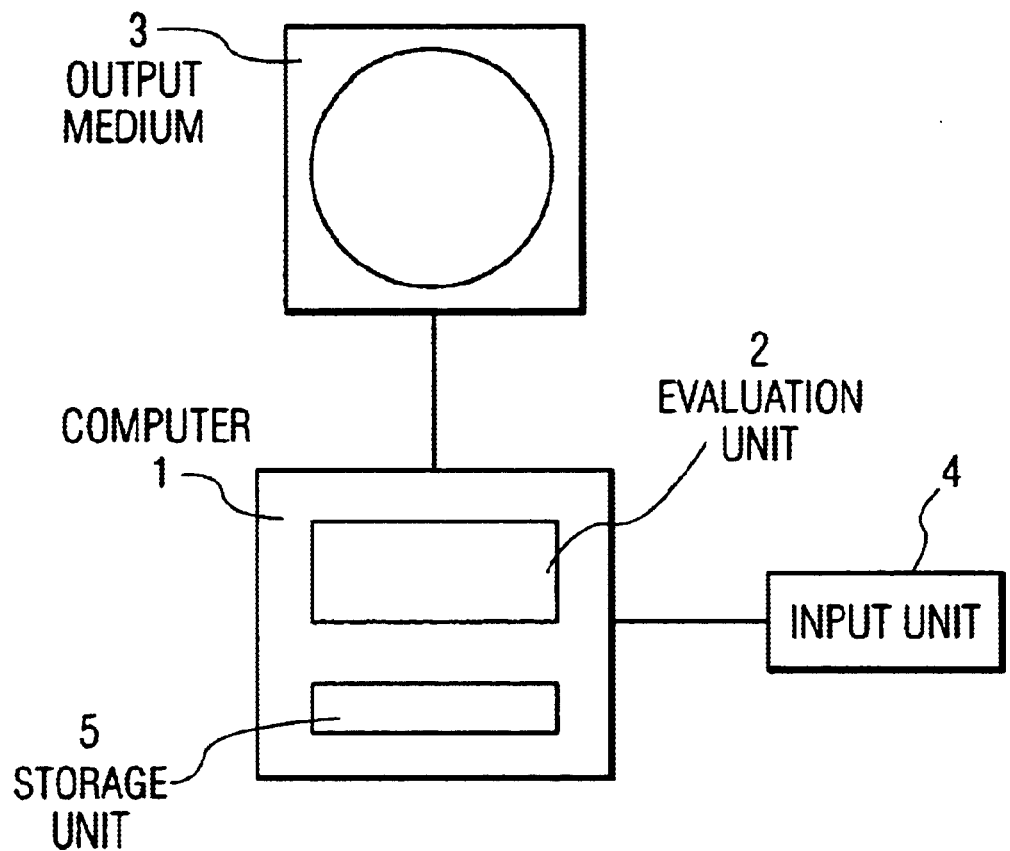
FIG. 1 is a schematic block diagram of the basic components of an inventive system.

FIG. 1 depicts the basic components of an inventive system, wherein the local arrangement of the basic components, as described below with reference to FIG. 2 and FIG. 3, can be arbitrary. That is, they need not be arranged at one and the same location. The system comprises a computing means 1 in the form of a computing or data processing means. An evaluation unit 2 is provided, by means of which the calculation and output of analytical data occurs. An output medium 3 in the form of a monitor or the like is allocated to a computer 1, at which it is possible to display the analytical data. There is also an input unit 4, which can be an input keyboard, via which the system user can answer the questions displayed to him or her at the output medium 3, though the input can of course also occur via the screen surface of the output medium 3, if this is a touch-screen.

A central element of this system is the evaluation unit 2. This is configured for the interrogation and acceptance of information entered at the user side and can function essentially in two distinct modes of operation. In one mode, predefined inquiries can be visualized to the user via the output medium 3, which he or she can answer with autonomously obtained facts. For example, different possible symptoms which are observable by the user are listed in the form of specific question blocks composed in the fashion of a menu, so that the user can then indicate that symptom which he observes himself, so that approximate primary information is already present. For example, the following choices can be given to the user: "skin rash," "runny nose," "headache," "aching joints," "stomachache." If one of these symptoms is present, which the user can detect himself without further difficulty, then the corresponding field or the corresponding key should be pressed. Depending on this result, another block of predefined questions can then be visualized. If, for example, the key "skin rash" is activated, then "pustules," "flaking" and "reddening" can be given as the next questions.

Additionally, the evaluation unit is fashioned for the autonomous formulation of specific interrogations of the system user, which are determined on the basis of the basic information which already exists or on the basis of additional entered information. To this end, an expert system is provided at the evaluation unit 2 side, to which a corresponding question selection module is allocated. The configuration in this regard is arbitrary. It is thus possible for problem-specific questions to be posed to the user, which the system can generate autonomously based on the existing information, in order to be able to collect information which is relevant to a well-grounded generation of analytical data. It is possible to select between the modes of operation of the evaluation unit 2 at the user side; i.e., the evaluation unit 2 first operates in the mode with the predefined inquiries, whereby it is capable of generating corresponding analytical data with the thus obtained information. For a more deeply grounded analysis, the user can then switch as needed to the mode of interactive inquiry with autonomous question formulation, whereby the generation of the questions is also based on the already existing information obtained in the other mode of operation.

Furthermore, as described above, the evaluation unit 2 is configured for rating the respective types of analysis with a value measure. This value measure can be calculated continuously between two extreme values. By means of this measure of value or probability, it is indicated to the user with what probability the analytical data for the concrete problem are valid. In the case of a medical problem, it can be indicated to the user in this way what percent chance there is that the disease which has been determined as the result of analysis could be present. Of course, several analytical results in the form of different diseases can be given, to which a separate measures of possibility are respectively given. For example, the following can be indicated to the user:

"Cold: 90%"
"Fever requiring treatment: 10%"
"Rhinitis: 30%",

These analytical data also can apply in an overlapping manner. The determination of the value measure can occur using fuzzy logic. Alternatively, the evaluation unit 2 can be configured for the calculation of the value or possibility measure based on a calculable probability or a probability interval. A probability value for the correctness of the analytical result or an interval, for instance 45–45% probability of presence, is calculated. For the probability calculation, the evaluation unit 2 is appropriately a causal network.

As for the formulation of the interrogation an expert system and an allocated question generating module can be provided for this purpose, as described. The formulation of the interrogation can occur based on an analytical calculation of the potential informational gain of the respective optionally formulatable inquiry. It is calculated analytically how the analytical data change given the posing of the optionally formulated inquiry, assuming one or more possible user responses. If the potential informational gain is great (that is, the analytical result that can be generated based on the information existing at the moment changes significantly in consideration of the possible user response), then the potential question is a relevant inquiry which should be made. If the analytical result does not change or does so only slightly, the possible question is of secondary importance.

The predefined inquiries can be presented as an output in hierarchically structured form and can be selectable and answerable incrementally at the user side, whereby they can be displayed, as described, in thematically ordered blocks, in the fashion of a question menu. The user thus has the option to be able to restrict the questions to a specific question.

The evaluation unit 2 also can be configured for the calculation and output of a weight designation with respect to the significance of the displayed inquiries. This weight designation indicates to the user how important the continuation of the data pickup is, in order to arrive at an authoritative analytical result. For example, the indications "high," "average," and "low" can be shown as an output according to inquiry. If the respective inquiry is characterized as a "high", then it can be recognized by the user that this is an important question which he or she should answer to the best of his or her knowledge, since this information enters into the analysis heavily. Very relevant inquiries are thus designated "high", while those whose answers do not affect the analytical result very much are designated "low". This assigning of potential significance designations should occur particularly given questions which are formulated by the evaluation unit 2 itself, since these are problem-specific questions which are formulated using the expert system and so using expert knowledge, which questions are directed to a specific problem in a concrete manner. The calculation of the weight designation can occur based on an analysis of the weighted reduction of the entropy in the evaluation unit 2 under the assumption of different items of response information that may be given in response to the respective inquiry. It is analyzed what an assumed response contributes in terms of clarification in the evaluation unit 2. This is structured such that, for each possible disease, a variety of symptoms are ranked and linked, and for instance each disease-symptom link is linked to a specific percentage of probability. It is now tested how the multitude of the original links with respect to one or more concrete diseases can be reduced, assuming a specific item of response information;

i.e., how the entropy of the links decreases given a significant, facilitative item of information that continues or remains constant, or increases given an item of information that is insignificant or disadvantageous for the analysis. The weighted reduction is thus analyzed; i.e., it is tested whether it is more advantageous to pose a question which is difficult to answer and has a high informational profit or one which is easy to answer and has a low informational profit. A specific algorithm is provided for the calculation of the weight designation.

As shown in FIG. 1, a storage unit 5 is provided. Only a single storage unit 5 is depicted in FIG. 1, though of course several can be provided. In this storage unit 5, user-specific information such as the age of the user, his disease history or the like can be filed. The evaluation unit 2 can automatically access this storage unit 5 and the information filed therein, or at least a part of this information. Alternatively or at the same time, this user-specific information can be at least partially released for acquisition only by the user, in order to avoid a random data access. Various password or security measures are available for this purpose.

Specific informational data for the analytical data also can be stored in the storage unit 5 or in another storage means (not illustrated), so that the data can be acquired and emitted as an output selectively. The data can be detailed explanations of a specific disease which is indicated as analytical data, it being possible for the user to have the data displayed as needed, if the user is interested in a more detailed description of the disease and possible causes, side effects and treatment options. The data forms an information database which can be accessed in case of need. An additional storage unit 5 can be further provided (it is also possible to utilize the storage means depicted in FIG. 1) in which the entered information can be filed and stored, so that the user can access it given a new inquiry without the information having to be entered again, which may be the case if the user notices the first signs of a disease and has primary analytical data calculated, and the user then has additional analysis performed at a later time, when the symptoms are manifested more clearly.

Besides this additional information, the user can request that the analytical data or at least a part of the information entered at the user side, on the basis of which the value measure was calculated, be shown as an output so that the user can see which of the given items of information were important and relevant to the analysis. So that it is not necessary to display all of the entered information that was employed in the calculation of the value measure, the evaluation unit 2 can be configured to select the output information by calculating a change of the value measure which would arise if a particular item of information were missing. It is thus analytically determined how the measures of value or possibility would be reduced from the present state, assuming the omission of an item of information. If a significant reduction occurs, then this is an important item of information, which should be displayed.

As described above, it is possible for the user to interrupt the operation at any time and have the analytical result displayed. To prevent a specific result from being generated on the basis of erroneous or clearly insufficient information, leading to misconception or incorrect action on the part of the user, the evaluation unit 2 can be configured for self-analysis such that, given a termination of the inquiry prompted at the user side, it is possible to check for the omission of one or more relevant items of information for the calculation of the analytical data and to allow the calculation result to be shown as an output, given the retrieval of one or more corresponding inquiries, only if warranted. The evaluation unit 2 thus itself checks whether it is capable of a sufficiently well-grounded generation of the analytical data on the basis of the existing information. If not, a preliminary calculation result can be displayed to the user, with simultaneous output of the relevant inquiry or inquiries needed to supply the omitted information, so that the user can answer these inquiries. When these inquiries are answered, the actual calculated, well-grounded analytical data can be made available as an output.

Figure 2:
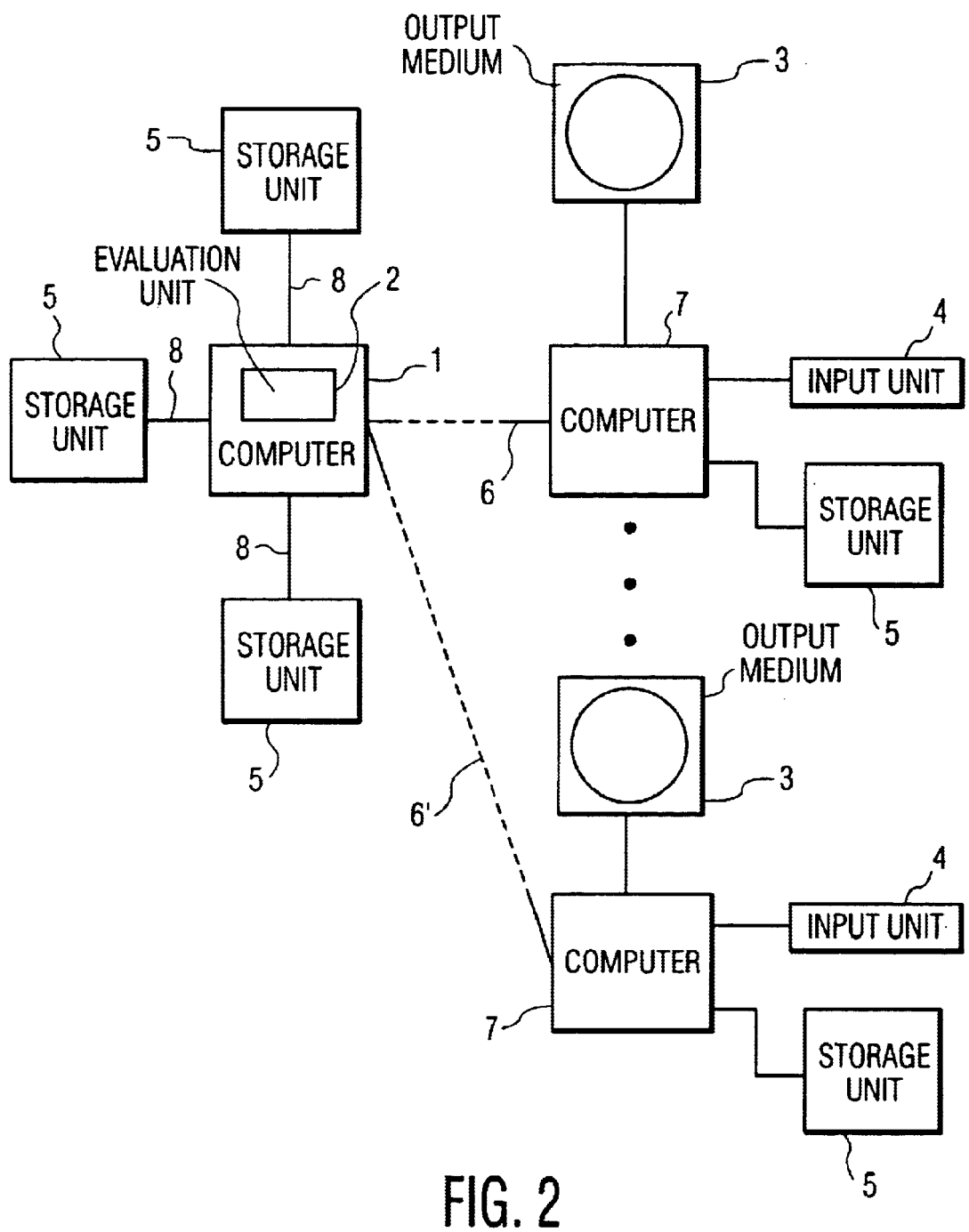
FIG. 2 is a schematic block diagram showing the basic components of a second embodiment of the inventive system with a remote computer and remote storage units.

FIG. 2 depicts another embodiment of an inventive system. A computer 1 with an evaluation unit 2 is provided in this embodiment as well. This computer 1 is arranged externally to the output medium 3 provided at the user side, in the fashion of a central server. The communication occurs via a communication channel 6, which can be a communication line or a wireless communication connection. An additional computer 7 with an allocated input unit 4 is provided at the user side.

Various storage units 5 are also allocated to the computer 1, which can be arranged externally to the computer 1 and communicate therewith via communication channels 8. These storage units 5 need not be arranged in the immediate environment of the computer, rather, they can be external databases fashioned in the manner of a central server, which the computer 1 can access as needed. One such storage unit 5 can be arranged at the office of a doctor who treats the system user, who is a patient of the doctor, for example. In this storage unit 5 provided at the doctor's office, a variety of user-specific data are already filed, which can be partially accessed and read out by the computer 1. According to FIG. 2, an additional storage unit 5 is also provided at the user side and communicates with the computer 7. Again, it is possible for user-specific data to be filed in this storage unit 5 which, like the previously described data, can either be read out by the computer 1 automatically, or can be released by the user, possibly upon request.

FIG. 2 also illustrates the capability for additional system subscribers to be linked to the system, which subscribers can also access the computer 1, via corresponding communication channels 6'.

Figure 3:
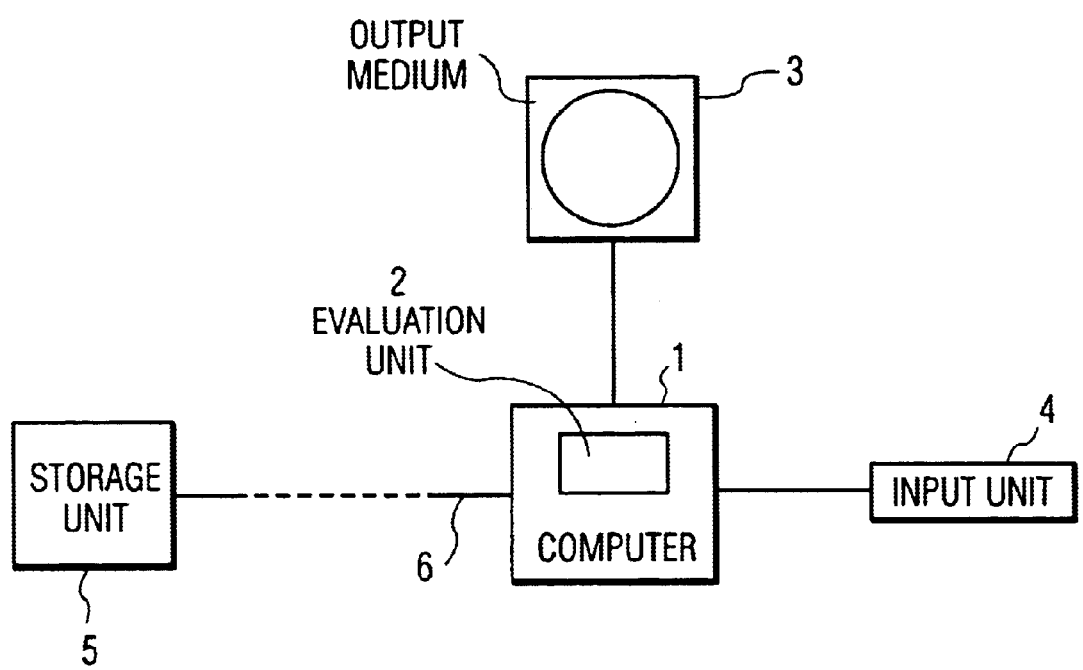
FIG. 3 is a schematic block diagram showing a further embodiment of the inventive system with remote storage units.

FIG. 3 depicts another embodiment of the inventive system. In this embodiment, both the computer 1 with the evaluation unit 2 and the output medium 3 are provided at the user side; only the storage unit 5 is arranged externally. This can be accessed via a communication channel of any type. Again, more than one storage unit 5 can be provided.

Although modifications and changes may be suggested by those skilled in the art, it is the intention of the inventors to embody within the patent warranted hereon all changes and modifications as reasonably and properly come within the scope of their contribution to the art.

We claim:

1. A computing system comprising:
   a computer including evaluation means for analyzing information which is entered into said computer and for generating analytical data based on said information;
   user input means for allowing a user to enter said information into said computer;
   an output means connected to said computer for displaying an output generated by said computer;
   said evaluation means comprising means for configuring and interrogating and accepting said information entered through said input means for organizing input of said information based on a plurality of inquiries produced by said evaluation means, said evaluation means selecting said inquires based on information entered in response to at least one previous inquiry, said inquiries being made available at said output means;

said evaluation means comprising means for controlling interactive acquisition of said information based on a running compilation of information for formulating and emitting said inquiries to said output means, and said evaluation means comprising means for processing information which is random in content and for producing a continuous value measure between two extreme values as a characterization of an analytical result based on said information, and said input means selectively providing said running information compilation on said output means at any time in response to receipt of a command from a user;

and a storage unit in which information entered via said input means is selectively filed and retrieved.

2. A system as claimed in claim 1 wherein said evaluation means is operable in a plurality of operating modes, and wherein an operating mode for said evaluation means can be set via said input means.

3. A system as claimed in claim 1 wherein said evaluation means comprises means for calculating said value measure from a calculation algorithm selected from the group consisting of fuzzy logic and probability algorithms.

4. A system as claimed in claim 1 wherein said evaluation means comprises means for formulating an inquiry based on an analytical calculation of a potential informational gain of the inquiry.

5. A system as claimed in claim 1 wherein said evaluation means comprises means for making predetermined inquiries available via said output means in a hierarchically structured form for incremental answering via said input means.

6. A system as claimed in claim 5 wherein said evaluation unit makes a plurality of predetermined inquiries available for common display in a question menu at said output means.

7. A system as claimed in claim 1 wherein said storage unit contains predetermined information related to a specific user.

8. A system as claimed in claim 7 wherein said evaluation unit has access to said information in said storage unit automatically.

9. A system as claimed in claim 7 wherein said evaluation means has access to said information in said storage unit upon output at said output means of an inquiry relating to said information stored in said storage unit.

10. A system as claimed in claim 1 wherein said evaluation means comprises means for making analytical data available at said output means in a plurality of forms.

11. A system as claimed in claim 1 further comprising a storage unit in which additional informational data, relative to said analytical data, are contained, said additional data being accessible by said evaluation means.

12. A system as claimed in claim 1 wherein said computer and said output means are disposed remote from each other.

13. A system as claimed in claim 1 wherein said computer and said output means are disposed together so as to be simultaneously accessible by a user operating said input means.

14. A system as claimed in claim 1 wherein said storage unit is disposed remote from said output medium.

15. A system as claimed in claim 1 wherein said storage unit is disposed remote from said computer.

16. A system as claimed in claim 1 wherein said storage unit is integrated in said computer.

17. A computing system comprising:

a computer including evaluation means for analyzing information which is entered into said computer and for generating analytical data based on said information;

user input means for allowing a user to enter said information into said computer;

an output means connected to said computer for displaying an output generated by said computer;

said evaluation means comprising means for configuring and interrogating and accepting said information entered through said input means for organizing input of said information based on a plurality of inquiries produced by said evaluation means, said evaluation means selecting said inquires based on information entered in response to at least one previous inquiry, said inquiries being made available at said output means;

said evaluation means comprising means for controlling interactive acquisition of said information based on a running compilation of information for formulating and emitting said inquiries to said output means, and said evaluation means comprising means for processing information which is random in content and for producing a continuous value measure between two extreme values as a characterization of an analytical result based on said information, and said input means allowing a user to retrieve, and have available as an output on said output medium, said running information compilation at any time;

and said evaluation means comprising means for calculating and emitting, at said output means, a weight designation identifying a significance of each inquiry shown at said output means, based on an analysis of a weighted reduction of entropy in said evaluation means dependent on response information which can be given in response to said inquiry.

18. A computer including evaluation means for analyzing information which is entered into said computer and for generating analytical data based on said information;

user input means for allowing a user to enter said information into said computer; an output means connected to said computer for displaying an output generated by said computer;

said evaluation means comprising means for configuring and interrogating and accepting said information entered through said input means for organizing input of said information based on a plurality of inquiries produced by said evaluation means, said evaluation means selecting said inquires based on information entered in response to at least one previous inquiry, said inquiries being made available at said output means;

said evaluation means comprising means for controlling interactive acquisition of said information based on a running compilation of information for formulating and emitting said inquiries to said output means, and said evaluation means comprising means for processing information which is random in content and for producing a continuous value measure between two extreme values as a characterization of an analytical result based on said information, and said input means allowing a user to retrieve, and have available as an output on said output medium, said running information compilation at any time;

and said evaluation means comprising means, upon entry of an interrogation termination via said input means, for determining whether a relevant item of information has been omitted from said running information compilation and for indicating said omission at said output means.

19. A system as claimed in claim 18 wherein said evaluation means comprises means for displaying a preliminary calculation result, with said relevant item of information omitted, at said output medium, and for simultaneously displaying an inquiry to obtain said relevant item of information.

20. A computing system comprising:

a computer including evaluation means for analyzing information which is entered into said computer and for generating analytical data based on said information;

user input means for allowing a user to enter said information into said computer;

an output means connected to said computer for displaying an output generated by said computer;

said evaluation means comprising means for configuring and interrogating and accepting said information entered through said input means for organizing input of said information based on a plurality of inquiries produced by said evaluation means, said evaluation means selecting said inquires based on information entered in response to at least one previous inquiry, said inquiries being made available at said output means;

said evaluation means comprising means for controlling interactive acquisition of said information based on a running compilation of information for formulating and emitting said inquiries to said output means, and said evaluation means comprising means for processing information which is random in content and for producing a continuous value measure between two extreme values as a characterization of an analytical result based on said information, and said input means selectively providing said running information compilation on said output means at any time in response to receipt of a command from a user;

and said evaluation means comprising means for making available, at said output means, at least a part of information entered said via input means on which said value measure is based, and means for calculating a change in said value measure which would occur if a selected item of information were omitted, and displaying an indication of said change of said value measure at said output means.

* * * * *